United States Patent
Frey et al.

(10) Patent No.: US 10,954,288 B2
(45) Date of Patent: Mar. 23, 2021

(54) MODIFIED ANTIBODY REGIONS AND USES THEREOF

(71) Applicant: BIOATLA, LLC, San Diego, CA (US)

(72) Inventors: Gerhard Frey, San Diego, CA (US);
Jay M. Short, Del Mar, CA (US);
Hwai Wen Chang, San Marco, CA (US)

(73) Assignee: BioAtla, Inc., San Diego, CA (US)

( * ) Notice: Subject to any disclaimer, the term of this patent is extended or adjusted under 35 U.S.C. 154(b) by 221 days.

(21) Appl. No.: 15/910,588

(22) Filed: Mar. 2, 2018

(65) Prior Publication Data

US 2018/0186863 A1 Jul. 5, 2018

Related U.S. Application Data

(63) Continuation of application No. 14/396,851, filed as application No. PCT/US2013/038538 on Apr. 26, 2013, now abandoned.

(60) Provisional application No. 61/639,729, filed on Apr. 27, 2012.

(51) Int. Cl.
*C07K 16/00* (2006.01)
*A61K 39/395* (2006.01)
*C07K 1/00* (2006.01)
*A61K 39/00* (2006.01)

(52) U.S. Cl.
CPC ........ *C07K 16/00* (2013.01); *A61K 2039/505* (2013.01); *C07K 2317/52* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 6,737,056 B1 | 5/2004 | Presta | |
| 7,217,797 B2 | 5/2007 | Hinton et al. | |
| 7,790,655 B2 | 9/2010 | Gao et al. | |
| 8,088,376 B2 | 1/2012 | Chamberlain et al. | |
| 2005/0014934 A1 | 1/2005 | Hinton et al. | |
| 2005/0037000 A1 | 2/2005 | Stavenhagen et al. | |
| 2005/0064514 A1 | 3/2005 | Stavenhagen et al. | |
| 2006/0104989 A1 | 5/2006 | Edwards et al. | |
| 2006/0173170 A1 | 8/2006 | Chamberlain et al. | |
| 2007/0036799 A1 | 2/2007 | Stavenhagen et al. | |
| 2009/0010920 A1 | 1/2009 | Lazar et al. | |
| 2009/0041770 A1 | 2/2009 | Chamberlain et al. | |
| 2010/0104564 A1 | 4/2010 | Hansen et al. | |
| 2010/0196362 A1 | 8/2010 | Stavenhagen et al. | |
| 2011/0081347 A1 | 4/2011 | Gorlatov | |
| 2011/0183412 A1 | 7/2011 | Hinton et al. | |
| 2012/0003210 A1 | 1/2012 | Farrington et al. | |
| 2013/0131319 A1 | 5/2013 | Igawa et al. | |

FOREIGN PATENT DOCUMENTS

| CN | 101189028 A | 5/2008 |
|---|---|---|
| EP | 2332985 A2 | 6/2011 |
| JP | 2006512087 A | 4/2006 |
| JP | 2013535944 A | 9/2013 |
| RU | 2517621 C2 | 5/2014 |
| WO | WO2005047327 A2 | 5/2005 |
| WO | WO2006019447 A1 | 2/2006 |
| WO | 2006053301 A2 | 5/2006 |
| WO | WO2006053301 A2 | 5/2006 |
| WO | WO2007021841 A2 | 2/2007 |
| WO | WO2010033279 A2 | 3/2010 |
| WO | WO2010085682 A2 | 7/2010 |
| WO | WO2010151792 A1 | 12/2010 |
| WO | 2011122011 A2 | 10/2011 |
| WO | WO2011122011 A2 | 10/2011 |
| WO | WO2012018790 A2 | 2/2012 |
| WO | WO2013010927 A1 | 1/2013 |

OTHER PUBLICATIONS

Extended European Search Report; dated Jan. 31, 2019 for EP Application No. 18209149.6.
Mexican 2nd Substantive Examination Requirement; dated Mar. 16, 2018 for MX Application No. MX/a/2014/012978.
Office Action for corresponding Brazilian Application No. BR112014026740-5; dated Oct. 15, 2019; (6 pages).
Yeung, Yik Andy, et al. "Engineering human IgG1 affinity to human neonatal Fc receptor: impact of affinity improvement on pharmacokinetics in primates." The Journal of Immunology 182.12 (2009): 7663-7671.
Canadian Office Action; dated Feb. 15, 2019 for CA Application No. 2,871,807.
Reasons for Final Rejection for corresponding Korean application No. 10-2014-7030719; dated Feb. 27, 2019 (11 pages).
Notification of Preliminary Rejection for Korean Patent Application No. 10-2014-7030719; dated Jul. 18, 2019.
JP Office Action; dated Oct. 2, 2018 for JP Application No. 2015-509206.
AU Examination Report; dated Aug. 23, 2018 for AU Application No. 2017225111.
International Preliminary Report on Patentability; dated Oct. 28, 2014 for corresponding PCT Application No. PCT/US2013/038538.
European Search Report; dated Aug. 19, 2015 for EP Application No. EP13781110.5.
Chinese Office Action; dated Jul. 11, 2016 for CN Application No. CN201380022401.0 along with an English abstract.
Chinese Office Action; dated Mar. 20, 2017 for CN Application No. CN201380022401.0.
Japanese Notice of Reasons for Refusal; dated Mar. 14, 2017 for JP Application No. JP201559206.
Dall'Acqua, William F., et al. "Increasing the affinity of a human IgG1 for the neonatal Fc receptor: biological consequences," The Journal of Immunology 169.9 (2002): 5171-5180.
Russian Office Action; dated Mar. 17, 2017 for RU Application No. RU2014147741.

(Continued)

*Primary Examiner* — Chun W Dahle

(74) *Attorney, Agent, or Firm* — Mendelsohn Dunleavy, P.C.

(57) ABSTRACT

The present invention relates to modified Fc regions of antibodies, and uses thereof, such as in antibodies that contain an Fc region of the present invention.

7 Claims, No Drawings

(56) References Cited

OTHER PUBLICATIONS

Datta-Mannan, Amita, et al. "Humanized IgG1 variants with differential binding properties to the neonatal Fc receptor: relationship to pharmacokinetics in mice and primates." Drug metabolism and disposition 35.1 (2007): 86-94.
Russian Office Action; dated Aug. 10, 2017 for RU Application No. RU2014147741.
Brown, John C., and Marian E. Koshland. "Activation of antibody Fc function by antigen-induced conformational changes." Proceedings of the National Academy of Sciences 72.12 (1975): 5111-5115.
Schlessinger, J., et al. "Antigen-induced conformational changes in antibodies and their Fab fragments studied by circular polarization of fluorescence." Proceedings of the National Academy of Sciences 72.7 (1975): 2775-2779.
Chames, Patrick, et al. "Therapeutic antibodies: successes, limitations and hopes for the future." British journal of pharmacology 157.2 (2009): 220-233.
EP Office Action; dated Oct. 4, 2017 for EP Application No. 13781110.5.
Second Chinese Office Action; dated Nov. 16, 2017 for CN Application No. 201380022401.0.
Mexican Office Action; dated Nov. 17, 2017 for Mexican Application No. MX/a/2014/012978.
Russian Office Action; dated Dec. 25, 2017 for RU Application No. RU2014147741.
Teillaud, Jean-Luc. "Antibody-dependent Cellular Cytotoxicity (ADCC)." eLS (2012).
Baker, Kristi, et al. "Neonatal Fc receptor for IgG (FcRn) regulates cross-presentation of IgG immune complexes by CD8-CD11b+ dendritic cells." Proceedings of the National Academy of Sciences 108.24 (2011): 9927-9932.
Non-Final Office Action; dated May 1, 2017 for U.S. Appl. No. 14/396,851.
Final Office Action; dated Dec. 5, 2017 for U.S. Appl. No. 14/396,851.
Japanese Final Decision on Refusal; dated Feb. 13, 2018 for JP Application No. 2015-509206.
Office Action from Canadian application No. 2,871,807; dated Jan. 28, 2020 (6 pages).
Dall'Acqua, William F. et al. "Properties of Human IgG1s Engineered for Enhanced Binding to the Neonatal Fc Receptor (FcRn)." Journal of Biological Chemistry 281.33 (2006): 23514-23524.
Communication pursuant to Article 94(3) EPC for corresponding European application No. 18209149.6; dated May 6, 2020 (5 pages).
1st Substantive Examination for corresponding Mexican application No. MX/a/2018/001914; dated Jul. 21, 2020 (8 pages).

MODIFIED ANTIBODY REGIONS AND USES THEREOF

RELATED APPLICATION INFORMATION

This application is a continuation of U.S. patent application Ser. No. 14/396,851 filed on Oct. 24, 2014, which is a 371 continuation of international application no. PCT/US2013/038538 filed on Apr. 26, 2013, designating the United States of America, which is a nonprovisional of U.S. provisional application No. 61/639,729 filed on Apr. 27, 2012.

BACKGROUND AND SUMMARY OF THE INVENTION

Considerable information has been published and is known about monoclonal antibodies and their utility in research, diagnosis, and in the treatment of multiple diseases, including cancer. Over a dozen monoclonal antibodies have government regulatory approval for therapeutic use in patients.

Antibodies with different properties (improved affinity, avidity and pharmacokinetics, for example) and structures, including fully human antibodies, chimeric antibodies with both human and non-human elements, Fab antibodies, and other antibody structures, have been constructed in the laboratory using molecular biology techniques, such as cloning, phage display, transgenic mice and mutagenesis. Goals of therapeutic antibody improvement include overcoming host anti-antibody responses and extending half-life of therapeutic antibodies, and there is a continuing need for improved antibodies.

The present invention pertains to modified Fc regions of antibodies, and uses thereof, such as in antibodies that contain a Fc region (e.g., in a full-length IgG antibody including full-length IgG1, IgG2, IgG3 or IgG4, a chimeric antibody, or a humanized antibody), or in a fusion protein that contains a Fc region, or a part of a Fc region (referred to as an "immunoglobulin (Ig) fusion protein", "Fc fusion protein", or "Fc fusion polypeptide"), of the present invention. Modified Fc regions of antibodies have been described in the art, including in U.S. Patent Application Number US2006/104989). The modified Fc regions of the present invention have a single amino acid substitution (also referred to as a Fc variant herein) at positions disclosed herein relative to the sequence of a corresponding unmodified (wild-type or parent) Fc region, and have one or more properties that differ from a corresponding unmodified Fc region as well as from other modified Fc regions that have been described in the art, such as increased binding to one or more Fc receptors and/or modified binding under different pH conditions. The modified Fc regions of the preset invention can be incorporated into any antibody or Fc fusion polypeptide using standard molecular biology techniques, and all such modified antibodies and Fc fusion polypeptides are intended to be encompassed by the invention. Fc refers to the last two constant region Ig domains of IgA, IgD, and IgG, and the last three constant region Ig domains of IgE and IgM, and the flexible hinge N-terminal to these domains. For IgA and IgM, Fc may include the J chain. Fc is bound by receptors, FcRs, which are present on certain cells. As the affinity of the interaction between Fc and certain FcRs present on particular cells correlates with targeted cytotoxicity, and clinical efficacy in humans correlates with the allotype of high or low affinity polymorphic forms of certain FcRs, an antibody or fusion polypeptide with a Fc region optimized for binding to one or more FcRs may result in more effective destruction of cancer cells.

In certain embodiments, the modified Fc regions of the present invention impart improved properties to a polypeptide or a complex which includes a polypeptide into which the Fc region is incorporated, e.g., a complex such as a full-length antibody, chimeric antibody or humanized antibody which includes an Ig heavy chain having an modified Fc region, such as increased or modified binding to one or more FcRs, and/or increased or modified antibody dependent cellular cytotoxicity (ADCC), as compared to a corresponding polypeptide or complex, such as an antibody, incorporating a corresponding unmodified (a wild-type or parent) Fc region, or a different modified Fc region. Thus, a corresponding polypeptide or antibody that lacks one or more of the Fc region modifications disclosed herein and differs in FcR binding as compared to a polypeptide or antibody incorporating a Fc region of the invention, may have a native (wild-type) Fc region sequence or may have a Fc region sequence with amino acid sequence modifications (such as additions, deletions and/or substitutions) other than those disclosed herein that result in increased or modified binding to at least one FcR. In some embodiments of the invention, modified Fc regions of the invention impart increased or decreased half life to a molecule.

In one embodiment of the invention, an modified Fc region of the invention contains one of the substitutions described herein. In other embodiments, an modified Fc region of the invention contains two, three, four, five or more substitutions described herein in combination, which may additively or synergistically enhance the properties of the modified Fc regions of the invention. In another embodiment, the invention includes a polypeptide having an modified Fc region of the invention, i.e., it is an Fc fusion polypeptide that contains one of the substitutions described herein. In one embodiment, the non-Fc region of the fusion polypeptide includes a target binding molecule. In other embodiments, the invention includes a polypeptide having an modified Fc region of the invention that contains two, three, four, five, six, ten, twelve, or more substitutions described herein in combination. In one embodiment, the invention includes an antibody or antigen-binding antibody fragment having an modified Fc region of the invention that contains one of the substitutions described herein. In other embodiments, the invention includes an antibody or antigen-binding antibody fragment having an modified Fc region of the invention that contains two, three, four, five, six, ten, twelve or more substitutions described herein in combination.

In another embodiment, the invention includes a polypeptide, e.g., one in a complex of polypeptides such as an antibody or an Fc fusion polypeptide, or a conjugate which includes a Fc region conjugated to another molecule (a Fc fusion conjugate), having an modified Fc region of the invention that contains one of the substitutions described herein. In other embodiments, the invention includes a polypeptide, e.g., one in a complex of polypeptides such as an antibody or a Fc fusion polypeptide, or a conjugate which includes a Fc region conjugated to another molecule, having an modified Fc region of the invention that contains two, three, four, five or more substitutions described herein in combination, as well as one or more other substitutions, which other substitutions may impart properties other than those associated with the substituted position(s) and/or substitutions in the modified Fc regions of the invention, or may additively or synergistically enhance the properties of the modified Fc regions of the invention. In some embodiments of the invention, a polypeptide with an modified Fc region of the invention has one or more of the functional properties described herein. For polypeptides with modified Fc regions of the invention that also include a non-FcR target binding molecule domain, which optionally together with other polypeptides may form an antibody, the target binding molecule domain or variable regions of the antibody may specifically bind virtually any target molecule or antigen. Accordingly, in one aspect, the invention pertains to a polypeptide having a Fc region (e.g., an IgG Fc region, such as an IgG1 Fc region) with the following amino acid substitution at the following amino acid residues (positions) in a Fc region: M252I, P257C, P257I, P257T, E258D, E258F, E258G, E258I, E258K, E258L, E258Q, E258S, E258V, E258W, V259E, V259G, V259I, V259R, T260A, T260C, T260F, T260L, T260N, T260S, T260W, S426C, S426N, V427S, V427T, M428F, M428Y, E430I, E430L, E430Q, A431F, A431H, A431P, H433A, H433E, H433R, N434A, N434D, N434F, N434G, N434H, N434I, N434M, N434R, N434V, N434W, N434Y, H435K, or these substitutions at any combination of those positions. For all positions discussed herein, numbering is according to the EU index as in Kabat (Kabat et al., 1991). Those skilled in the art of antibodies will appreciate that this convention consists of non-sequential numbering in specific regions of an Ig sequence, enabling a normalized reference to conserved positions in Ig families. Thus, the positions of any given Ig as defined by the EU index will not necessarily correspond to its sequential sequence.

In addition to the polypeptide, protein or other complex, e.g., a conjugate, incorporating an modified Fc region of the invention described herein, the invention also encompasses polynucleotides and expression vectors encoding an modified Fc region or polypeptides having an modified Fc region, including libraries of those polynucleotides and expression vectors, host cells into which such polynucleotides or expression vectors have been introduced, for instance, so that the host cell produces a polypeptide having the modified Fc region, libraries of host cells, and methods of making, culturing or manipulating the host cells or libraries of host cells. For instance, the invention includes culturing such host cells so that a polypeptide with a modified Fc region is produced, e.g., secreted or otherwise released from the host cell. Pharmaceutical compositions and kits which include a polypeptide, protein or other complex with an modified Fc region of the invention, and/or polynucleotides, expression vectors or host cells encoding polypeptides having such an modified Fc region, are also encompassed. Moreover, use of a polypeptide, protein or conjugate with an modified Fc region of the invention, such as in Fc receptor binding assays or to induce ADCC activity in vitro or in vivo, is also encompassed by the invention. The invention also provides a polypeptide, protein, conjugate, polynucleotide, expression vector, and/or host cell of the invention for use in medical therapy, as well as the use of a polypeptide, protein or other complex, polynucleotide, expression vector, and/or host cell of the invention for the manufacture of a medicament, e.g., useful to induce ADCC activity in vitro or in vivo.

An antibody, as used herein, is a protein having one or more polypeptides encoded by all or part of mammalian Ig genes, including polyclonal or monoclonal antibodies, which specifically binds to one or more Fc receptors (FcRs), and, if one or more variable regions are present, the protein binds to an antigen, which protein is optionally glycosylated. A full-length antibody has a structure corresponding to the natural biological form of an antibody found in nature including variable and constant regions. For example, a full-length antibody may be a tetramer, generally with two identical pairs of two Ig chains, each pair having one light chain and one heavy chain. Each light chain includes immunoglobulin domains VL and CL, and for IgG, each heavy chain includes immunoglobulin domains VH and CH, where CH includes Cγ1, Cγ2, and Cγ3. In humans, Ig genes include kappa (κ) and lambda (λ) light chain genetic loci and heavy chain genetic loci, which include constant region genes mu (μ), delta (δ), gamma (γ), sigma (σ), and alpha (α) for the IgM, IgD, IgG, IgE, and IgA isotypes, respectively.

An antibody further, as used herein, unless otherwise specified, includes full-length antibodies and fragments thereof, including naturally occurring antibodies, chimeric antibodies, recombinant antibodies including humanized antibodies, or antibodies subjected to other in vitro alterations, and antigen binding fragments thereof.

A "parent Fc", as used herein, can be a naturally occurring Fc region of an IgA, IgD, IgE, IgG or IgM class of antibody. Alternatively, the source of a parent Fc is a Fc region from a naturally occurring antibody, including IgG1, IgG1, IgG3, IgG4, IgA1, or IgA2. A parent Fc region to be modified may be selected for its FcR binding affinity and/or FcR binding pattern, and an modified Fc region of the invention has at least an enhanced affinity for at least one FcR, but may otherwise have the same pattern of FcR binding, as the parent Fc region.

A parent Fc region is preferably one that interacts with one or more FcRs, including but not limited to FcγRs, FcαRs, FcμRs, FcδRs, FcRn, and viral FcγR. An modified Fc region of the invention derived from such a parent Fc region is one that has an enhanced interaction with one or more FcRs and enhanced ADCC, relative to the parent Fc region. ADCC generally requires the Fc region to be combined with a binding domain (e.g., an antibody variable domain). Methods to detect FcR binding and ADCC are known to the art.

FcRs are defined by their specificity for immunoglobulin isotypes and are well known in the art.

An Fc containing fusion includes a polypeptide where a Fc region with favorable FcR binding, and optionally favorable pharmacokinetics, is linked to one or more molecules. The linkage may be synthetic in nature, e.g., via chemical conjugation, or via recombinant expression, i.e., a fusion polypeptide is formed. Thus, the molecule linked to a Fc region may be a molecule useful to isolate or purify the Fc region, e.g., a tag such as a Flag-tag, Strep-tag, glutathione S transferase, maltose binding protein (MBP) or a His-tag, or other heterologous polypeptide, e.g., a ligand for a receptor, an extracellular domain of a receptor, or a variable region of a heavy Ig chain, and/or another molecule.

Once a vector encoding an modified Fc region of the invention or Fc region containing polypeptide such as an Ig heavy chain with an modified Fc region or other Fc fusion polypeptide, the vector may be introduced into a host cell, optionally along with other vectors, e.g., a vector encoding an Ig light chain, or into a host cell modified to express another polypeptide such as an Ig light chain, or into an in vitro transcription/transcription reaction, so as to express the encoded polypeptide. The modified Fc region, Ig heavy chain and Ig light chain may also be expressed in the same vector and introduced into a host cell. For some expression systems, host cells may be cultured in conventional nutrient media modified as appropriate for inducing promoters, selecting transformants, or amplifying desired sequences. A resulting polypeptide with an modified Fc region is optionally isolated, e.g., from host cell supernatants, and screened for one or more activities.

In one embodiment, the Fc region may be one that is anchored to the surface of a cell, such as a host cell, e.g., via fusion with a transmembrane domain.

Suitable host cells for expressing the polynucleotide in the vectors are the prokaryotic, yeast, or higher eukaryotic cells. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis, Pseudomonas* such as *P. aeruginosa*, and *Streptomyces*. Eukaryotic microbes such as filamentous fungi or yeast are also suitable cloning or expression hosts for polypeptide variant-encoding vectors. *Saccharomyces cerevisiae, Schizosaccharomyces pombe, Kluyveromyces* hosts such as, e.g., *K. lactis, K. fragilis, K. bulgaricus, K. wickeramii, K. waltii, K. drosophilarum, K. thermotolerans*, and *K. marxianus; Pichia pastoris, Candida, Trichoderma reesia, Schwanniomyces* such as *Schwanniomyces occidentalis*; and filamentous fungi such as *Neurospora, Penicillium, Tolypocladium*, and *Aspergillus* hosts may be employed. Suitable host cells for the expression of glycosylated polypeptides are derived from multicellular organisms. Examples of invertebrate cells for expression of glycosylated polypeptide include plant and insect cells. Examples of eukaryotic cell generation, screening and production hosts include 3T3 mouse fibroblast cells, BHK21 Syrian hamster fibroblast cells, MDCK, dog epithelial cells, Hela human epithelial cells, PtK1 rat kangaroo epithelial cells, SP2/0 mouse plasma cells, and NSO mouse mouse plasma cells, HEK 293 human embryonic kidney cells, COS monkey kidney cells, CHO, CHO-S Chinese hamster ovary cells, R1 mouse embryonic cells, E14.1 mouse embryonic cells, H1 human embryonic cells, H9 human embryonic cells, PER C.6, and human embryonic cells. Numerous baculoviral strains and variants and corresponding permissive insect host cells from hosts such as *Spodoptera frugiperda, Aedes aegypti, Aedes albopictus, Drosophila melanogaster*, and *Bombyx mori* may be used. For instance, viral vectors maybe used to introduce a polynucleotide of the invention, particularly for transfection of *Spodoptera frugiperda* cells. Plant cell cultures of cotton, corn, potato, soybean, petunia, tomato, and tobacco can also be utilized as hosts. Examples of useful vertebrate cells include mammalian cells, e.g., human, simian, canine, feline, bovine, equine, caprine, ovine, swine, or rodent, e.g., rabbit, rat, mink or mouse cells, such as CHO cells. Transgenic plants and animals may be employed as expression systems, although glycosylation patterns in those cells may be different from human glycoproteins. In one embodiment, transgenic rodents are employed as expression systems. Bacterial expression may also be employed. Although bacterially expressed proteins lack glycosylation, other alterations may compensate for any reduced activity such as poor stability and solubility, which may result from prokaryotic expression.

Optionally, an Fc region or Fc containing polypeptide is isolated from host cells, e.g., from host cell supernatants, or an in vitro transcription/translation mixture, yielding a composition. An isolated polypeptide in the composition is one which has been isolated from at least one other molecule found in host cells, host cell supernatants or the transcription/translation mixture, e.g., by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography. For some applications, the isolated polypeptide in the composition is the predominant species present (i.e., on a molar basis it is more abundant than any other individual species in the composition), and preferably comprises at least about 50 percent (on a molar basis), more preferably more than about 85%, about 90%, about 95%, and about 99, of all macromolecular species present. The isolated Fc region or Fc containing polypeptide may be subjected to further in vitro alterations, e.g., treated with enzymes or chemicals such as proteases, molecules such as those which alter glycosylation or ones that are useful to conjugate (couple) the isolated Fc region or Fc region containing polypeptide to another molecule such as a label including but not limited to fluorescent labels (e.g., FITC, rhodamine, lanthanide, phosphors), enzymatic labels (e.g., horseradish peroxidase, /3-galactosidase, luciferase, alkaline phosphatase), chemiluminescent labels, biotinyl groups, avidin groups, or polypeptide epitopes recognized by a secondary reporter (e.g., leucine zipper pair sequences, binding sites for secondary antibodies, metal binding domains, epitope tags), sugars, lipids, fats, paramagnetic molecules or sound wave emitters, metals, or synthetic polymers.

Methods to screen for activities associated with polypeptides or complexes that incorporate a Fc region, including but not limited to FcR binding (see, for example, U.S. Pat. Nos. 6,737,056, 7,217,797, 8,088,376, all incorporated herein by reference), are well known to the art. For instance, to assess ADCC activity of a Fc containing polypeptide, an in vitro and/or in vivo ADCC assay, may be performed using varying effector:target ratios, e.g., PBMC and NK cells or in a animal model, respectively. In one embodiment, Fc containing polypeptides expressed by host cells are screened for enhanced FcR receptor binding affinity or activity in vitro and/or in vivo and/or ADCC activity in vitro and/or in vivo. In one embodiment, the binding of a FcR by a Fc containing polypeptide with an modified Fc region of the present invention is greater than the binding of that receptor by a corresponding polypeptide with an unmodified Fc region. Thus, by introducing amino acid sequence modifications described herein in a wild-type or parent Fc region or a Fc region containing polypeptide, which wild-type or parent Fc region preferably elicits ADCC and optionally is a human Fc region, e.g., a native sequence human Fc region human IgG sequence, a modified Fc region is obtained which binds FcR with better affinity and mediates ADCC in the presence of human effector cells more effectively than the wild-type or parent Fc region or Fc region containing polypeptide. Soluble FcRs such as recombinant soluble human CD 16 and recombinant soluble human CD32 can be contacted with one or more different modified Fc regions in parallel, and modified Fc regions having one or more substitutions that enhance binding to human CD16 but not to human CD32, relative to an unmodified Fc region, are identified. Those substitutions may be combined with other substitutions that enhance binding. A combination of substitutions of the present invention in an Fc region or Fc region containing polypeptide may yield a combinatorially modified Fc region, or a combinatorially modified Fc region containing polypeptide with synergistically enhanced properties.

Other methods to identify polypeptides with modified Fc regions, including antibodies with an modified Fc region, with desirable properties, and thus a corresponding polynucleotide sequence, which method may be employed alone or in combination with methods described above, include using modeling, e.g., 3D-modeling, of modified Fc regions, preferably in the context of the molecule to be screened for activity, e.g., an antibody with the Fc region, to select for Fc regions with particular characteristics. Characteristics that may be screened for by modeling include, but are not limited to, a particular angle near FcR binding sites, hinge architecture, intra- and inter-molecular chain interactions, e.g., substitutions that promote or disrupt hydrophobic interactions or stabilize conformation in a particular region. Thus, a 3D model of a Fc region containing polypeptide having at least one of the substituted positions of the invention in combination with one or more other substitutions may be employed to identify combinations of substitutions to be introduced into a polynucleotide for expression in host cells.

The Fc variants of the present invention, whether or not incorporated into a heterologous polypeptide, e.g., incorporated into a Fc fusion with a ligand for a cell surface receptor, e.g., CTLR-4 ligand or heavy chain of an antibody, or conjugated to a molecule of interest, as well as polynucleotides and host cells encoding those variants, optionally in combination with one or more other agents, e.g., therapeutic or research reagents, are useful in a variety of methods, e.g., in screening methods, prophylactic methods, therapeutic methods, veterinary methods and agricultural methods. The one or more other agents include other Fc region or Fc region containing polypeptides, including those with unmodified Fc regions. In one embodiment, an Fc variant is incorporated into an antibody or other Fc fusion polypeptide and that antibody or Fc fusion polypeptide, optionally in conjunction with one or more other useful compositions, employed to target particular cells. In one embodiment, an Fc variant containing antibody or an antigen-binding fragment thereof targets and optionally kill target cells that bear the target antigen. In another embodiment, a Fc variant containing antibody or an antigen-binding fragment thereof targets and activates cells that bear the target antigen, e.g., thereby increasing expression of another antigen, such as a viral or cellular antigen. In one embodiment, the Fc variants or polypeptides incorporating an Fc variant of the present invention may be used to prevent, inhibit or treat various conditions or diseases, in humans and non-humans, including non-human mammals. For example, an antibody containing an modified Fc region of the invention may be administered to a human or non-human animal which is at risk of, e.g., prone to having a disease, prior to the onset of the disease and so prevent or inhibit one or more symptoms of that disease. A Fc region or Fc region containing polypeptide, or a conjugate thereof, may be administered after clinical manifestation of a disease in a human or non-human animal to inhibit or treat the disease. In one embodiment, a pharmaceutical composition comprising an antibody or Fc fusion polypeptide of the present invention is administered to a human or non-human animal with an autoimmune, immunological, infectious, inflammatory, neurological, or neoplastic disease, e.g., cancer. Fc regions or Fc region containing polypeptides of the invention may be administered alone or in combination with one or more other therapeutic agents, including but not limited to cytotoxic agents, e.g., chemotherapeutic agents, cytokines, growth inhibitory agents, anti-hormonal agents, kinase inhibitors, anti-angiogenic agents, cardioprotectants, or other therapeutic agents, in amounts that are effective for the purpose intended. The skilled medical practitioner can determine empirically the appropriate dose or doses of therapeutic agents including Fc regions or Fc region containing polypeptides of the present invention that are may thus be administered concomitantly with one or more other therapeutic regimens. For example, an antibody or Fc fusion polypeptide of the present invention may be administered to a patient along with chemotherapy or other therapy, e.g., other agents such as an anti-angiogenic agent, a cytokine, radioisotope therapy, or both chemotherapy and other therapies. In one embodiment, the antibody or Fc fusion of the present invention may be administered in conjunction with one or more other antibodies or Fc fusions, which may or may not comprise a Fc variant of the present invention. In one embodiment, a Fc containing polypeptide of the present invention is administered with a chemotherapeutic agent, i.e., a chemical compound useful in the treatment of cancer. A chemotherapeutic or other cytotoxic agent may be administered as a prodrug, i.e., it is in a form of a pharmaceutically active substance that is less cytotoxic to cells compared to the drug and is capable of being converted into the drug.

Pharmaceutical compositions are also contemplated having an Fc region, an Fc fusion polypeptide, antibodies having a Fc region, or conjugates thereof, that are formulated, optionally with one or more other agents. Formulations of antibodies, Fc regions, or Fc region containing polypeptides, or conjugates, of the present invention are prepared for storage by mixing the antibodies, Fc regions, or Fc region containing polypeptides, or conjugates, having the desired degree of purity with optional pharmaceutically acceptable carriers, excipients or stabilizers (Remington's Pharmaceutical Sciences 16th edition, Osol, A. Ed., 1980), in the form of lyophilized formulations or aqueous solutions. Acceptable carriers, excipients, or stabilizers are nontoxic to recipients at the dosages and concentrations employed, and include buffers such as antioxidants; alkyl parabens; low molecular weight (less than about 10 residues) polypeptides; hydrophilic polymers; amino acids; monosaccharides; and other carbohydrates; chelating agents; fillers; binding agents; additives; coloring agents; salt-forming counterions; metal complexes; and/or non-ionic surfactants. Other formulations includes lipid or surfactant based formulations, microparticle or nanoparticle based formulations, including sustained release dosage formulations, which are prepared by methods known in the art.

The concentration of the Fc region, antibody or other Fc region containing polypeptide of the present invention in the formulation may vary from about 0.1 to 100 weight %. In a preferred embodiment, the concentration of the Fc region, antibody or Fc fusion polypeptide is in the range of 0.001 to 2.0 M. In order to treat a patient, an effective dose of the Fc region, or antibody or other Fc region containing polypeptide, and conjugates thereof, of the present invention may be administered. By "therapeutically effective dose" herein is meant a dose that produces the effects for which it is administered. Dosages may range from 0.01 to 100 mg/kg of body weight or greater, for example 0.1, 1, 10, or 50 mg/kg of body weight, with 1 to 30 mg/kg being preferred, although other dosages may provide beneficial results. The amount administered is selected to prevent treat a particular condition or disease. Administration of the Fc region, or antibody or other Fc region containing polypeptide, and conjugates thereof, of the present invention maybe continuous or intermittent, depending, for example, upon the recipient's physiological condition, whether the purpose of the administration is therapeutic or prophylactic, and other factors known to skilled practitioners. The administration of the Fc region, or antibody or other Fc region containing polypeptide, and conjugates thereof, of the present invention may be essentially continuous over a preselected period of time or may be in a series of spaced doses. Both local and systemic administration is contemplated.

Administration of the pharmaceutical composition comprising a Fc region, an antibody or other Fc containing polypeptide and conjugates of the present invention, preferably in the form of a sterile aqueous solution, may be done in a variety of ways, including, but not limited to, orally, subcutaneously, intravenously, intranasally, intraotically, transdermally, topically, intraperitoneally, intramuscularly, intrapulmonary, inhalable technology, vaginally, parenterally, rectally, or intraocularly. In some instances, for example for the treatment of wounds, inflammation, etc., the antibody or Fc fusion may be directly applied as a solution or spray.

EXAMPLE 1

Analysis of FcRn Binding of Clones. FcRn binding is assessed by determining the fold difference in binding as compared to wild type antibody with an unmodified Fc; binding can be measured as published (for example, see Dall'Acqua, et al., The Journal of Biological Chemistry, Vol 281, Num 33, 23515-23524 (2006)). All modified Fcs of the present invention were shown to bind FcRn at pH 7.4 with the same binding as unmodified control Fc regions. All modified Fcs of the present invention were shown to bind FcRn at pH 6.0 with 2 to 80 fold binding as compared to unmodified control Fc regions.

Modified Fc regions with changes in binding to human FcRn may result in changes in the half-lives of immunoglobulins containing the modified Fc regions. Engineering antibodies with modified half lives may have benefit for therapeutic applications, including antibodies with increased half lives that prolong activity and antibodies with decreased half lives that increase clearance of antibodies with undesirable prolonged exposure properties, such as radiolabeled antibodies.

REFERENCES

Molecular Cloning: A Laboratory Manual (Sambrook et al, 3rd Ed., Cold Spring Harbor Laboratory Press, (2001).
Harlow and Lane, Antibodies: A Laboratory Manual Cold Spring Harbor Laboratory Press, New York, 1988
Kabat et al., Sequences of Proteins of Immunological Interest, 5th Ed., United States Public Health Service, National Institutes of Health, Bethesda (1991)
Carter et al., Nucleic Acids Res., 13:4431 (1985)
Kunkel et al., Proc. Natl. Acad. Sci. USA, 82:488 (1987)
Higuchi, in PCR Protocols, pp. 177-183 (Academic Press, 1990)
Vallette et al., Nuc. Acids Res., 17:723 (1989) Wells et al., Gene, 34:315 (1985)
Gazzano-Santoro et al., J. Immunol. Methods, 202:163 (1996)
Green et al., Nature Genet., 7:13 (1994)
Lonberg et al., Nature, 368:856 (1994)
Taylor et al., Int. Immun, 6:579 (1994)
McCafferty et al., Nature, 348:552 (1990)
Johnson and Chiswell, Current Opinion in Structural Biology, 3_:5564 (1993)
Dall'Acqua, et al., The Journal of Immunology, 169:5171-5180 (2002)
Yeung, et al., The Journal of Immunology, 182:7663-7671 (2009)
Zalevsky, et al., Nature Biotechnology; doi: 10.1038/nbt.1601 (published online 17 Jan. 2010)
Dall'Acqua, et al., The Journal of Biological Chemistry, Vol 281, Num 33, 23515-23524 (2006)

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

All documents, including but not limited to publications, patents and patent applications, cited herein are herein incorporated by reference.

We claim:

1. An antibody comprising a modified IgG Fc region, wherein the modified IgG Fc region has only a single amino acid substitution relative to a parent IgG Fc region selected from E258F and V427T,
   wherein the numbering of positions in the parent IgG Fc region is that of the EU index as in Kabat in the Fc region.
2. The antibody of claim 1, wherein the amino acid substitution is E258F.
3. The antibody of claim 1, wherein the amino acid substitution is V427T.
4. The antibody of claim 1, wherein the parent IgG Fc region comprises a human IgG Fc region.
5. A composition comprising an antibody of claim 1 and a pharmaceutically acceptable carrier, an excipient or a stabilizer.
6. The antibody of claim 1, wherein the antibody has an increased half life, in comparison with an antibody having the parent IgG Fc region.
7. The composition of claim 5, wherein the antibody comprises an amount of from about 0.1 to 100 wt. % of the composition.

* * * * *

UNITED STATES PATENT AND TRADEMARK OFFICE
CERTIFICATE OF CORRECTION

PATENT NO. : 10,954,288 B2
APPLICATION NO. : 15/910588
DATED : March 23, 2021
INVENTOR(S) : Frey et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 270 days.

Signed and Sealed this
Thirty-first Day of January, 2023

Katherine Kelly Vidal
*Director of the United States Patent and Trademark Office*